United States Patent [19]

Kleemann et al.

[11] Patent Number: 4,562,153

[45] Date of Patent: Dec. 31, 1985

[54] PROCESS FOR THE SEPARATION OF L-LEUCINE AND L-ISOLEUCINE

[75] Inventors: Axel Kleemann, Hanau; Jürgen Martens, Alzenau; Horst Weigel, Rodenbach, all of Fed. Rep. of Germany

[73] Assignee: Degussa Aktiengesellschaft, Frankfurt, Fed. Rep. of Germany

[21] Appl. No.: 612,803

[22] Filed: May 22, 1984

[30] Foreign Application Priority Data

May 25, 1983 [DE] Fed. Rep. of Germany ....... 3318933

[51] Int. Cl.$^4$ .......................... C12P 13/06; C07P 41/00
[52] U.S. Cl. ...................................... 435/116; 435/280
[58] Field of Search .................................. 435/116, 280

[56] References Cited

U.S. PATENT DOCUMENTS 3,841,966  10/1974  Soichiro et al. ..................... 435/280
4,259,441   3/1981  Bauer ................................. 435/116

FOREIGN PATENT DOCUMENTS 2741081  3/1979  Fed. Rep. of Germany .

Primary Examiner—Lionel M. Shapiro
Attorney, Agent, or Firm—Cushman, Darby & Cushman

[57] ABSTRACT

The separation of L-leucine and L-isoleucine in aminoacid mixtures containing at least 30 weight percent L-leucine, at most 70 weight percent L-isoleucine and at most 40 weight percent of other aminoacids is accomplished by acetylating the mixture, precipitating the acetylation product by acidification, subjecting the aqueous solution to a saponification by an L-aminoacid acylase until 25 to 95% of the N-acetyl-L-leucine is saponified, crystallizing pure L-leucine from the saponification mixture and separating it off, isolating N-acetyl-L-isoleucine from the mother liquor and saponifying it in known manner to the free aminoacid and isolating the free aminoacid.

8 Claims, No Drawings

PROCESS FOR THE SEPARATION OF L-LEUCINE AND L-ISOLEUCINE

BACKGROUND OF THE INVENTION

The invention is directed to a process for the separation of L-leucine and L-isoleucine in aminoacid mixtures (i.e. aminocarboxylic acid mixtures) which contain 30 to 65 weight percent L-leucine, 35 to 70 weight percent L-isoleucine, and at most 35 weight percent of other aminoacids, in each case based on the dry material.

The aminoacids leucine and isoleucine have the same empirical formula $C_6H_{13}NO_2$ and differ only through the structure of the branched aliphatic side chain R:

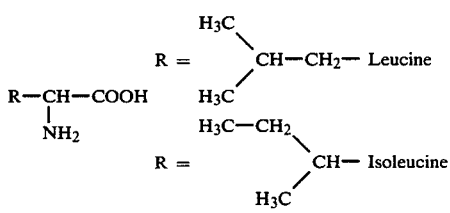

Because of their very similar structural characteristics these aminoacids show very similar properties in their physical and chemical behavior and their separation presents great difficulties.

The first separation of leucine and isoleucine was carried out via the copper complexes. In that case the dried copper complexes of the aminoacids were extracted with methanol, the copper salt of isoleucine thereby dissolves. In a similar process the cobalt complexes of the aminoacids were also separated by extraction with alcohol. However, with these processes there arises the problem of the recovery of the metals and the further purification of the aminoacids.

Other authors described the separation of leucine and isoleucine with aromatic sulfonic acids. Thus there were proposed the use of 2-bromotoluene-5-sulfonic acid or naphthalene-2-sulfonic acid for the precipitation of leucine and 1-chloro-4-naphthalene-sulfonic acid or 2-naphthol-6-sulfonic acid for the precipitation of isoleucine. Benzenesulfonic acid as well as p-toluenesulfonic acid were also employed for the separation of leucine and isoleucine. In these processes the precipitate must be purified by numerous recrystallizations and a particular problem is created by the separation of the precipitation agent which is frequently strongly toxic.

In a further known process mixtures of isoleucine, leucine and valine are separated through a multistep crystallization of L-leucine in the pH range 1.5 to 2.0 and subsequently L-isoleucine hydrochloride is obtained by crystallization from concentrated hydrochloric acid, in which case the mother liquor becomes enriched with residual leucine. However, according to this process, there cannot be obtained l-leucine in sufficient purity for pharmaceutical uses.

SUMMARY OF THE INVENTION

The process of the invention comprises:
(a) acetylating the aminoacid mixture (i.e. the aminocarboxylic acid mixture) in known manner,
(b) precipitating a mixture of N-acetylaminoacids enriched in N-acetyl-L-leucine and N-acetyl-L-isoleucine from the crude mixture of acetylation products by acidifying with a mineral acid,
(c) subjecting this enriched mixture in aqueous solution having a total concentration between 0.1 and 1.5 moles/l of acetylaminoacids at a pH between 6 and 8 and a temperature between 10° and 40° C. in the presence of an effector to a hydrolysis by a L-aminoacid acylase until 25 to 95% of the N-acetyl-L-leucine is saponified to the free aminoacid,
(d) crystallizing pure L-leucine from the crude hydrolysis mixture and separating from L-leucine,
(e) isolating N-acetyl-L-isoleucine from the mother liquor remaining after the separation of the L-leucine, and
(f) hydrolyzing the N-acetyl-L-leucine to the free aminoacid in known manner.

As starting materials for the process of the invention there can be used mixtures of aminoacids which consist of only leucine and isoleucine. Likewise, however, there can also be used other aminoacid mixtures, which besides contain other aminoacids, e.g. aminocarboxylic acids. Such mixtures of aminoacids are obtained in the processing of protein sources, such as desugared molasses, cereal seeds or corn seeds, oil residues, microorganisms, especially yeast, or casein, as well as keratin (hair, bristles, feathers, horn shavings) and leather.

In the hydrolysis such sources of protein frequently accumulate as difficulty soluble residues which are rich in leucine and isoleucine. Likewise there are obtained from the hydrolysate in chromatographic processes (ion exchange, ion exclusion and/or molecular sieve effect) fractions which are rich in leucine and isoleucine. Such fractions besides can still contain impurities, especially inorganic salts such as sodium chloride, sodium sulfate, ammonium chloride, or ammonium sulfate.

There are especially suited for the process of the invention aminoacid mixtures which contain 40 to 65 weight percent leucine, 35 to 60 weight percent isoleucine and a maximum of 20 weight percent of other aminoacids.

The aminoacid mixture is first acetylated in known manner. The acetylation can be carried out with acetyl chloride or acetic anhydride or even with ketone according to the process known from German OS 2741081.

Subsequently a mixture of N-acetylaminoacids is precipitated from the crude mixture of acetylation products by acidification with a mineral acid, e.g. hydrochloric acid or sulfuric acid,. It is appropriate to acidify until a pH value between 0.5 and 2 is reached. Thereby there already occurs an enrichment of N-acetyl-L-leucine and N-acetyl-L-isoleucine. The content of N-acetylaminoacids other than N-acetyl-L-leucine and N-acetyl-L-isoleucine which may be present is reduced. Through a subsequent recrystallization from water, an aliphatic alcohol having 1 to 4 carbon atoms and miscible with water, such as methanol, ethanol, n-propanol, iso-propyl alcohol, n-butanol, isobutyl alcohol or t-butyl alcohol or a mixture of water and such an alcohol, there can normally be reduced the content of other N-acetylaminoacids to less than 4, in many cases to less than 1 weight percent based on the dried material.

The mixture enriched in N-acetyl-L-leucine and N-acetyl-L-isoleucine is then subjected to a saponification by an L-aminoacid acylase. The adjustment of the pH to the range between 6 and 8 for example, can be carried out with ammonia, but preferably there is used sodium hydroxide liquor. As effectors there can be added those customarily added in the resolution of N-acetyl-DL-α-amino-carboxylic acids by means of an L-aminoacid acylase, for example, the ions $Ca^{2+}$, $Fe^{2+}$, $Mn^{2+}$, $Mg^{2+}$, $Zn^{2+}$, and preferably $Co^{+2}$. They are suitably employed in a concentration between $1\times10^{-5}$ and $1\times10^{-1}$ moles/l and for example, in the form of the corresponding chloride. In many cases it is advantageous to add to the reaction mixture additional small amounts of a biocide, especially p-hydroxybenzoic acid n-propyl ester.

As L-aminoacid acylase there is preferably employed a renal acylase. It can be used either in the commercial native form or as an immobilizate on organic carriers such as cross-linked agarose, dextran gels, cellulose, hydroxyethyl cellulose or mixed polymerizates of acrylamide with cross-linking comonomers, or on inorganic carrier materials such as various porous oxidic materials or especially glass beads.

The reaction time needed for the hydrolysis can be shortened by using a relatively large amount of L-aminoacid acylase. Making allowance for longer reaction times the amount of L-aminoacid acylase added can be reduced considerably. Accordingly there is a marked relationship between the reaction time and the amount of L-aminoacid acylase employed.

The hydrolysis, thus reaction step (c) is ceased when 25 to 95%, preferably 30 to 85%, especially 50 to 80% of the N-acetyl-L-leucine originally present is hydrolyzed to the free L-leucine. The hydrolysis reaction is followed analytically, e.g. by means of a high pressure liquid chromatography or with an aminoacid analyzer.

The hydrolysis reaction can be carried out discontinuously or continuously. For the discontinuous reaction, the process is carried out with a stirring kettle or in a tank with recirculation. A continuous reaction is carried out for example by means of an enzyme-membrane reactor.

If the mixture employed for the saponification reaction has a relatively high concentration of N-acetyl-L-leucine, for example, between 1.0 and 1.5 moles/l then after a short time, there begins to crystallize out a colorless precipitate, which precipitate consists of pure L-leucine. If the mixture is employed in lower concentrations, it is suitable to concentrate the crude hydrolysis mixture under careful conditions, in which case pure L-leucine also crystallizes out. In both cases, the pure L-leucine is isolated by filtering off or centrifuging, in a given case, after previous classification for the purpose of separating off a immobilized L-aminoacid acylase which may have been employed.

If the hydrolysis is carried out with native L-aminoacid acylase, then after the separation off of the L-leucine by ultra-filtration the L-aminoacid acylase can be recovered, e.g. on a hollow fiber membrane, and employed again.

It can be advantageous in some circumstances to isolate the L-leucine in several fractions, i.e. after separation of a first fraction continuing the hydrolysis and obtaining further fractions of L-leucine. A further purification of individual fractions or of the entire amount of separated off L-leucine which is desirable in a given case, can be carried out by recrystallization from water.

The N-acetyl-L-isoleucine is noticeably enriched in the mother liquor remaining after separation of the L-leucine and in a given case, of the L-aminoacid acylase. This can be isolated in a known manner by extraction, for example, with ethyl acetate, fractional crystallization or by means of an ion exchanger. The free aminoacids L-leucine and L-isoleucine normally likewise still contained in the mother liquor can be recovered and again returned to the acetylation step.

Finally, the N-acetyl-L-isoleucine is hydrolyzed in known manner, e.g. with hydrochloric acid, to the free aminoacid. This can be further purified through crystallization as the hydrochloride. The purified hydrochloride then is converted into the pure-L-isoleucine by means of a weakly basic ion exchanger or by dissolving in ethanol and neutralizing with a tertiary amine, for example, triethylamine.

Compared to the known processes for the separation of leucine and isoleucine the process of the invention has a further substantial advantage. In the hydrolysis of proteins operated on an industrial scale, there occurs a partial racemization of the L-leucine. If the L-leucine is obtained according to the process of the invention then the product obtained has a higher optical purity, since the enantisospecific acylase only catalyzes the hydrolysis of N-acetyl-L-aminoacid while the N-acetyl-D-aminoacids remain behind unchanged.

The invention is further explained in the following examples. The following applies to these examples:

The activity of the L-aminoacid acylase is given in units (U). 1U at a pH of 7.0 and 25° C. hydrolyzes 1 μ-mole of N-acetyl-L-methionine per hour.

The rotary value $[\alpha]_D^{25}$ given for the L-leucine and the L-isoleeucine was measured at C=4 in 6N hydrochloric acid. The rotary value of the pure aminoacids in pharmaceutical quality according to the U.S. Pharmacopoeia XX under these conditions is:

L-Leucine $[\alpha]_D^{25} = +14.9°$ to $+17.3°$

L-Isoleucine $[\alpha]_D^{25} = +38.9°$ to $+41.0°$

The determination of the composition of the aminoacid starting mixtures was made with an aminoacid analyzer.

The determination of the composition of the aminoacid of the mixture of N-acetylaminoacids employed for the enzymatic samponification is carried out via the rotary value.

Unless otherwise indicated, all parts and percentages are by weight.

The process can comprise, consist essentially of, or consist of the recited steps with the stated materials.

EXAMPLE 1

A fraction of neutral aminoacids obtained from the chromatographic separation of a keratin hyrolysate as a brown powder had the following composition of aminoacids:

Leu—49.8%,
Ile—36.1%,
Val—3.5%,
Met—3.5%,
Tyr—2.5%,
Ala—2.1%,
Phe—1.6%,
Gly—0.9%.

525 grams of this mixture were dissolved in 2 liters of 2N aqueous sodium hydroxide and cooled to 0° C. Within 1 hour there were stirred in 410 ml of acetic anhydride and simultaneously 850 ml of 5N of aqueous sodium hydroxide, whereby attention was paid that the pH remained in the region between 10 and 12 and the temperature did not exceed +5° C. After addition was ended the mixture was stirred for 1 more hour at 50° C.

The brown solution was stirred with concentrated hydrochloric acid until there was reached pH 1.5.

By filtering with suction, washing with water and drying there was obtained 530 grams of acetyl compounds as a pale brown colored powder. This crude product was recrystallized from n-butanol whereby there were obtained 335 grams of a colorless mixture of 65% N-acetyl-leucine and 35% N-acetyl-isoleucine.

86.6 grams of this mixture of N-acetyl-leucine and N-acetyl-isoleucine were dissolved in 500 ml of 1N aqueous sodium hydroxide. By addition of a few drops of aqueous sodium hydroxide the pH was adjusted to 7.5.

As catalyst there was added 500 mg of acylase from pig kidneys (1200 U/mg) and 60 mg of $CoCl_2 \times 6H_2O$.

The clear solution was heated to 38° C. After three hours the first crystals formed. After 9 hours the mixture was cooled to 20° C. and the voluminous precipitate was filtered off with suction. After washing with water and drying there were obtained 19.3 grams of pure L-leucine having a rotary value of $[\alpha]_D^{25} = +16.2°$. The filtrate was stationary for 24 hours at 20° C. whereby crystals separated off anew. This mixed fraction of 14.6 grams having a rotary value (degree of rotation) $[\alpha]_D^{25} = +17.4°$ was separated and returned again to the process.

The filtrate was acidified with concentrated hydrochloric acid to pH 1 and extracted with 300 ml of ethyl acetate in 2 portions. The organic phase was evaporated to dryness under reduced pressure and there was obtained a colorless residue of 15.3 grams of N-acetyl-isoleucine.

This residue was stirred with 25 ml of concentrated hydrochloric acid and 15 ml of water for 3 hours at 100° C. for deacetylization. Then it was cooled to 10° C. and the crystallized isoleucine-hydrochloride was isolated by filtering with suction. This hydrochloride was dissolved in 200 ml of water and led through a column containing 70 ml of a weakly basic anion exchanger (Lewatit MP 62). After washing with water, concentrating of the eluate at reduced pressure to a thick crystal magma and filtering with suction there was obtained 9.3 grams of pure L-isoleucine having a rotary value of $[\alpha]_D^{25} = +40.3°$.

EXAMPLE 2

A fraction of neutral aminocarboxylic acids which was obtained by chromatographic separation of a protein hydrolysate and subsequent fractional crystallization had the following composition:

Leu—43%,
Ile—56%,
Val—1%.

525 grams of this mixture was dissolved in 2 liters of 2N aqueous sodium hydroxide and cooled to 0° C. Within one hour there were stirred in 410 ml of acetic anhydride and simultaneously 850 ml of 5N sodium hydroxide, whereupon thereafter care was taken that the pH remained in the region of 10–12 and the temperature of +5° C. was not exceeded. After ending the addition stirring was continued for one more hour at 5° C.

There was established a pH of 1.6 with semi-concentrated sulfuric acid.

After filtering with suction, washing with water and drying there were obtained 553 grams of solid material. This was recrystallized from aqueous methanol, whereby there were obtained 480 grams of a colorless mixture of 50% N-acetyl-leucine and 50% N-acetyl-isoleucine.

86.6 grams of this mixture of equal parts of N-acetyl-leucine and N-acetyl-isoleucine were suspended in 400 ml of water and adjusted to pH 7.0 with 50% aqueous sodium hydroxide. There were added 50 mg of $CoCl_2 X6H_2O$ and 50 mg of commerical pig kidney acylase (1200 U/mg) and the mixture was filled up to 500 ml with water. The clear solution was stirred at 36° C. for 6 hours. By filtering with suction, washing and drying there were obtained 17.9 grams of pure L-leucine having a rotary value of $[\alpha]_D^{25} = +15.9°$.

The filtrate was allowed to stand overnight at 20° C., whereby a further 9.0 grams of crystals separated out. The rotary value was $[\alpha]_D = +21.0°$.

This mixed fraction was separated off and returned again to the process. The filtrate obtained was treated with hydrochloric acid until a pH of 1 was reached and then was extracted with ethyl acetate. The organic phase was evaporated and the residue (24.6 grams) was heated with 40 ml of concentrated hydrochloric acid and 25 ml of water for 3 hours at 100° C. Then clear solution was cooled to 10° C. and the crystallized L-isoleucine hydrochloride filtered off with suction.

By dissolving the hydrochloride in ethanol and neutralizing with triethylamine there were obtained 15.9 grams of pure-L-isoleucine having a rotary value $[\alpha]_D^{25} = +40.2°$.

The entire disclosure of German priority application P 3318933.1 is hereby incorporated by reference.

What is claimed is:

1. A process of separating L-leucine and L-isoleucine in an aminocarboxylic acid mixture containing 30 to 65 weight percent L-leucine, 35 to 70 weight percent L-isoleucine and at most 35 weight percent of other aminocarboxylic acids, in each case based on the dry material comprising:
    (a) acetylating the aminoacid mixture,
    (b) precipitating a mixture of N-acetylaminoacids enriched in N-acetyl-L-leucine and N-acetyl-L-isoleucine from the crude mixture of acetylation products,
    (c) subjecting this enriched mixture in aqueous solution having a total concentration between 0.1 and 1.5 moles/l of acetylaminoacids at a pH between 6 and 8 and a temperature between 10° and 40° C. in the presence of an catalyst to hydrolysis by a L-aminoacid acylase until 25 to 95% of the N-acetyl-L-leucine is hydrolyzed to the free aminoacid,
    (d) crystallizing pure L-leucine from the crude hydrolysis mixture and separating the L-leucine,
    (e) isolating N-acetyl-L-isoleucine from the the mother liquor remaining after the separation of the L-leucine, and
    (f) hydrolyzing the N-acetyl-L-isoleucine to the free aminoacid.

2. A process according to claim 1 including the step of recrystallizing the mixture of N-acetylamino acids precipitated in step (b) from water, a water miscible aliphatic alcohol having 1 to 4 carbon atoms or a mixture of water and such an alcohol before proceeding with step (c).

3. A process according to claim 2 wherein the effector is the ions $Ca^{2+}$, $Fe^{2+}$, $Mn^{2+}$, $Mg^{2+}$, $Zn^{2+}$, or $Co^{2+}$.

4. A process according to claim 3 wherein the effector is employed as the chloride salt.

5. A process according to claim 4 wherein the salt is CoCl$_2$.

6. A process according to claim 1 wherein the effector is the ions Ca$^{2+}$, Fe$^{2+}$, Mn$^{2+}$, Mg$^{2+}$, Zn$^{2+}$, or Co$^{2+}$.

7. A process according to claim 6 wherein the effector is employed as the chloride salt.

8. A process according to claim 7 wherein the salt is CoCl$_2$.

* * * * *